US006538133B1

(12) United States Patent
Aoki et al.

(10) Patent No.: US 6,538,133 B1
(45) Date of Patent: Mar. 25, 2003

(54) PROCESS FOR PRODUCING XYLITOL OF HIGH PURITY

(75) Inventors: Yuuichi Aoki, Kawasaki (JP); Eriko Ono, Kawasaki (JP); Kazutaka Nagashima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/631,351

(22) Filed: Aug. 2, 2000

(30) Foreign Application Priority Data

Aug. 10, 1999 (JP) .......................................... 11-226712
Aug. 10, 1999 (JP) .......................................... 11-226713

(51) Int. Cl.$^7$ ............................ C07H 1/06; C12P 19/00; C12P 19/02
(52) U.S. Cl. ........................... 536/127; 435/41; 435/72; 435/105
(58) Field of Search ............................ 536/127; 435/41, 435/72, 105

(56) References Cited

U.S. PATENT DOCUMENTS

| 4,008,285 | A |   | 2/1977 | Melaja et al. |
| 5,081,026 | A | * | 1/1992 | Heikkila et al. ............. 435/158 |
| 5,084,104 | A | * | 1/1992 | Heikkila et al. ............. 127/46.2 |
| 6,086,681 | A | * | 7/2000 | Lindroos et al. ............. 127/37 |

FOREIGN PATENT DOCUMENTS

| EP | 0 421 882 | 4/1991 |
| EP | 0 754 758 | 1/1997 |
| GB | 1 413 032 | 11/1975 |
| WO | WO 97/49658 | 12/1997 |

OTHER PUBLICATIONS

Derwent Publications, AN 1994–002177, JP 05 308 984, Nov. 22, 1993.

* cited by examiner

Primary Examiner—James O. Wilson
Assistant Examiner—Devesh Khare
(74) Attorney, Agent, or Firm—Oblon, Spivak, McClelland, Maier & Neustadt, P.C.

(57) ABSTRACT

Herein are disclosed a process for producing xylitol of high purity (one-step desalting process) which comprises the steps of (1) removing the solid matter from a culture froth obtained by culturing a xylitol-producing microorganism in an aqueous culture medium, (2) desalting the resulting solid matter-removed culture broth by removing the ionic substances therefrom by means of a cation-exchange resin and an anion-exchange resin, (3) subjecting the resulting desalted solution to the chromatography using a strongly acidic cation-exchange resin to separate the xylitol from the other sugar alcohol(s) and sugar(s), and (4) obtaining the xylitol by separating it at a high purity from the resulting xylitol solution (fraction), and to a similar process (two-step desalting process) but wherein the desalting carried out twice by adding the ion-exclusion step between Steps (1) and (2) of the above-mentioned process, whereby most of the ionic substances are removed, by which processes highly pure xylitol can be obtained from a xylitol solution in a commercially effective way, in the method for producing xylitol by using a xylitol-producing microorganism.

17 Claims, 1 Drawing Sheet

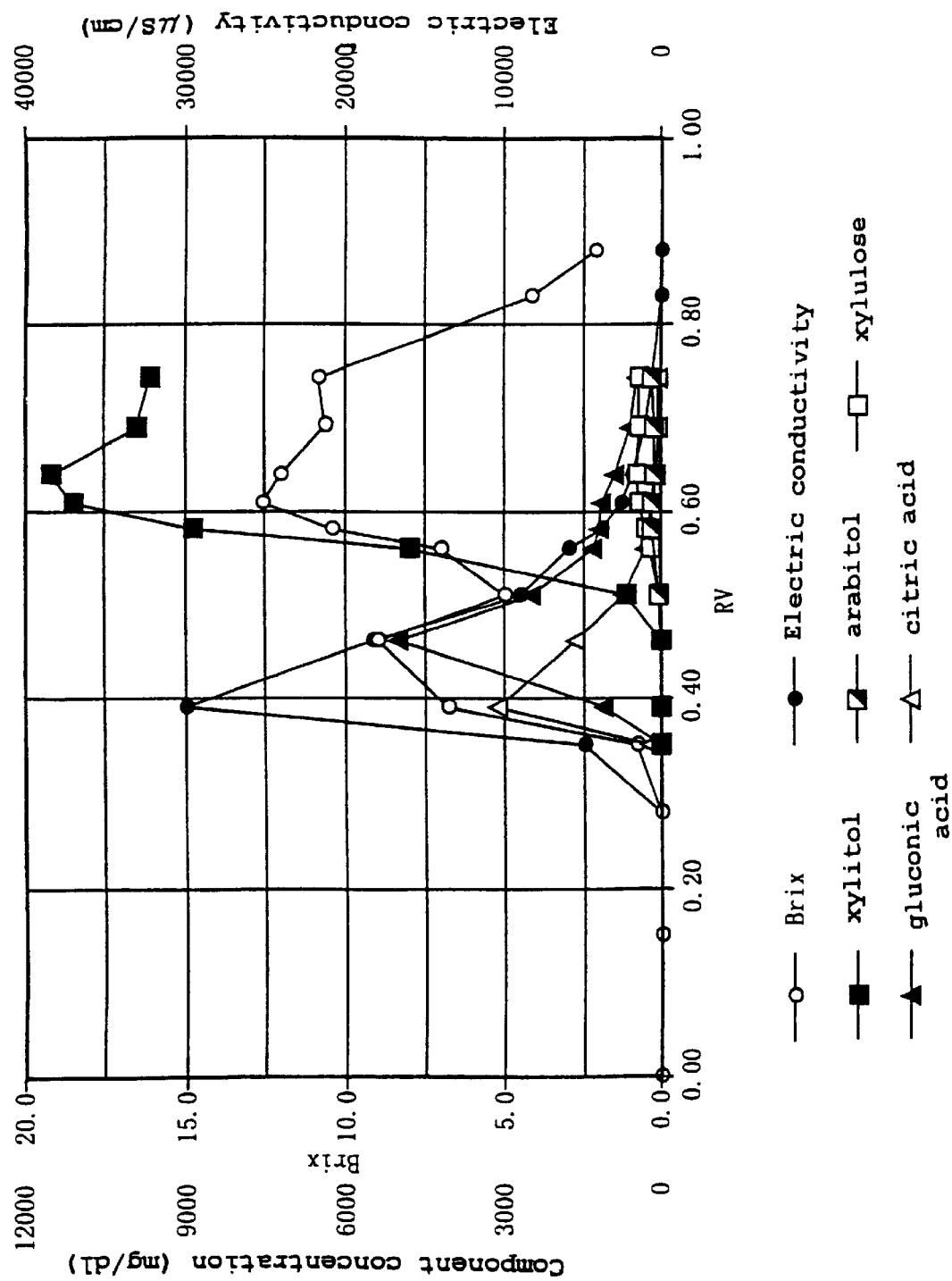

PROCESS FOR PRODUCING XYLITOL OF HIGH PURITY

BACKGROUND OF THE INVENTION

1. [Technical Field to which the Invention Belongs]

The present invention relates to a method of producing xylitol, particularly to a process for producing a highly pure xylitol product by which xylitol can be obtained by separating it in high purity from a culture broth of a xylitol-producing microorganism (e.g., a xylitol enzymatic reaction broth or a xylitol fermentation broth) by ingeniously utilizing ion-exchange resins.

2. [Prior Art]

Xylitol is widely present also in nature, and is a naturally occurring sweetener contained also in fruits and vegetables such as strawberry, cauliflower, lettuce, and spinach. Xylitol has a property of a lower calorific value though it exhibits a sweetness level comparable to sucrose. In addition, it has an excellent property, i.e., an anti-dental caries property.

Xylitol is, as disclosed in U.S. Pat. No. 4,008,825, produced mainly by reduction of xylose which is, in turn, obtainable through hydrolysis of xylan contained in plant materials. In this method, since the content of xylan in plant materials is low, there exist problems that th e yield of xylose resulting from such hydrolysis is low and, in addition, that many impurities such as other pentoses and hexsoses accompany the xylose. Furthermore, generation of plenty of liquid wastes during the hydrolysis and much cost of treating the liquid wastes for conserving the environment are other problems.

Xylose thus obtained is then converted to xylitol through reduction in the presence of a catalyst. When the xylose is reduced, the above-mentioned impurities such as other pentoses and hexsoses accompanying the xylose are reduced concurrently with the xylose, and converted into sugar alcohols having a structure resembling xylitol. Therefore, as disclosed in Japanese Patent Application Laid-Open (Kokai) No. 2690/1980, Japanese Patent Publication (Kokoku) Nos. 15054/1986, and 35169/1983, and the like, it is necessary to separate the contaminant many kinds of sugar alcohols from the aimed-at xylitol.

Accordingly, it is desirable to separate xylose from a hydrolysate of xylan as purely as possible. Low purity xylose may complicate steps required for purification of xylitol obtained by reduction of xylose, and, as a result, lead to increase of the cost of producing xylitol.

For solving the problem, it is desired to develop a method for producing xylitol where the starting material is easily available, and wastes are only generated in a small amount as well as the cost is inexpensive.

As such a method, it is investigated to produce xylitol from easily available glucose using a microorganism, without intervening xylose as an intermediate. For example, Published Japanese Translation of PCT International Publication for Patent Application No. 505522/1996 discloses a method for producing xylitol from glucose, using a yeast.

A method for producing xylitol from glucose, using a microorganism, can eliminate relatively severe conditions and danger accompanying hydrolysis of xylan contained in plant materials and hydrogenation of xylose using a metal catalyst, while enabling to produce xylitol under mild conditions. As a result, it leads to reduction of the cost for production.

Xylitol formed by microorganisms, however, may be accompanied with organic acids (for example, citric acid, acetic acid, gluconic acid, fumaric acid and malic acid) as by-products, and sugars and sugar alcohols (for example, glucose, D-arabitol, and glycerol) as by-products. It is also accompanied with some medium components and components derived from the microorganisms. Therefore, it is difficult to obtain xylitol having a high purity when the culture broth of a xylitol-producing microorganism (a xylitol enzymatic reaction broth or a xylitol fermentation broth) is, as it is, concentrated to crystallize the xylitol. Furthermore, the aforementioned Published Japanese Translation No. 505522/1996 refers indeed to purification of xylitol obtained by fermentation, but there are disclosed no concrete procedures for purifying the xylitol. And, other than the publication, any procedures for purification of xylitol are not known for methods of producing xylitol, starting with glucose with the use of a microorganism. For these reasons, if highly pure xylitol can be recovered from a xylitol-containing solution produced by using a microorganism (a xylitol fermentation broth or a xylitol enzymatic reaction broth), it means that xylitol can be easily obtained in a commercially inexpensive way.

SUMMARY OF THE INVENTION

Problems to be Solved by the Invention

An object of the present invention is to provide a means for obtaining highly pure xylitol in a commercially effective way from a xylitol solution (a culture broth of a xylitol-producing microorganism, e.g., a xylitol enzymatic reaction broth, or a xylitol fermentation broth), in the method for producing xylitol by using a xylitol-producing microorganism.

Means for Solving the Problems

As a result of extensive studies on production method of highly pure xylitol, the present inventors have found that highly pure xylitol can be obtained from a culture broth of a xylitol-producing microorganism such as a xylitol enzymatic reaction broth or a xylitol fermentation broth, by utilizing ion exchange resins ingeniously, and have accomplished the present invention based on such findings.

Accordingly, the present invention relates to a process for producing xylitol of high purity which comprises the steps of (1) removing the solid matter from a culture froth obtained by culturing a xylitol-producing microorganism in an aqueous culture medium, (2) desalting the resulting solid matter-removed culture broth by removing the ionic substances therefrom by means of a cation-exchange resin and an anion-exchange resin, (3) subjecting the resulting desalted solution to the chromatography using a strongly acidic cation-exchange resin to separate the xylitol from the other sugar alcohol(s) and sugar(s), and (4) obtaining the xylitol by separating it at a high purity from the resulting xylitol solution (fraction), and to a similar process but wherein the desalting carried out twice by adding the ion-exclusion step between Steps (1) and (2) of the above-mentioned process, i.e., a process for producing xylitol of high purity which comprises the steps of (1) removing the solid matter from a culture broth obtained by culturing a xylitol-producing microorganism in an aqueous culture medium, (2a) desalting the resulting solid matter-removed culture broth by removing most of the ionic substances therefrom by means of the ion-exclusion chromatography using a strongly acidic cation-exchange resin, (2b) desalting the solution resulting from the ion-exclusion chromatography (partially desalted solution) by removing the remaining ionic substances therefrom by means of a cation-exchange resin and an anion-exchange resin, (3) subjecting the resulting desalted solution to the chromatography using a strongly acidic cation-exchange resin to separate the xylitol from the other sugar alcohol(s) and sugar(s), and (4) obtaining the xylitol by separating it at a high purity from the resulting xylitol solution (fraction).

BRIEF DESCRIPTION OF THE DRAWINGS

FIG. 1 shows an ion-exclusion chromatogram by using a cation-exchange resin, "UBK-550" (Step (2a) in Example 3).

DETAILED DESCRIPTION OF THE INVENTION

The following will explain the present invention in greater detail.

A xylitol enzymatic reaction broth or a xylitol fermentation broth to be treated according to the present invention can be obtained, for example, by culturing a xylitol-producing microorganism, Gluconobacter oxydans ATCC 621, in a culture medium containing D-arabitol to convert the D-arabitol contained in the medium into xylitol (enzymatic reaction). D-Arabitol can be, in turn, formed from glucose fermentatively by a known migrobiological method as described in, for example, Can. J. Microbiol., 31 (1985), 467–471. The D-arabitol thus formed can be used, after being separated from the fermentation broth or in the form of such resulting fermentation broth without separation, as a culture medium for a xylitol-producing microorganism (medium for enzymatic reaction). Anyway, xylitol is finally produced by enzymatic reaction or fermentation with a xylitol-producing microorganism.

Since the culture broth of a xylitol-producing microorganism (a xylitol enzymatic reaction broth or a xylitol fermentation broth) thus obtained contains mirobial cells and other insoluble components (solid matter), the solid matter is first removed by suitable means such as centrifugation (Step(1)).

The resulting solid matter-removed culture broth thus obtained contains, as impurities, unreacted starting raw materials (unmetabolized starting raw materials), intermediary sugars and sugar alcohols, by-products such as organic acids, and inorganic salts added as culture medium components. When such impurities are to be removed, the ionic substances including organic acids are first carried out, i.e., desalting is first conducted. If it is tried, e.g., to separate the xylitol by crystallization from such a xylitol enzymatic reaction broth or fermentation broth, without previously desalting, concentration of such broth followed by addition of xylitol seed crystals may not result in crystallization of xylitol or, even if it crystallizes out, the yields are remarkably lowered.

Such ionic substances can be removed from a xylitol solution, e.g., by passing it through a cation-exchange resin such as "SK-1B" manufactured by Mitsubishi Chemical Corporation, and through an anion-exchange resin such as "WA30" manufactured by the same company (Step(2)).

The resulting desalted solution contains, though most of the total solid or solid content is xylitol, non-ionic impurities such as unreacted starting raw materials or unmetabolized starting raw materials, and intermediary sugars and sugar alcohols in small amounts. Therefore, these impurities are separated by chromatography using a strongly acidic cation-exchange resin (Step(3)).

For this chromatographic separation, a strongly acidic cation-exchange resin, for example, "UBK-555" manufactured by Mitsubishi Chemical Corporation can be used, preferably in the Ca-form. A xylitol solution to be subjected to such chromatographic separation should have a solid content concentration of 10 to 100 g/dl, preferably 30 to 50 g/dl (when the concentration of a given xylitol solution to be treated is out of the range, the concentration is adjusted so as to get to within the range by dilution or concentration), and is loaded in an amount of 5 to 20%, preferably 5 to 10%, based on the quantity of the resin. Such chromatographic separation fractionates a xylitol solution into a xylitol fraction and a fraction of sugars and other sugar alcohols. The fraction of sugars and other sugar alcohols may be, if desired, returned to a step for conversion thereof into xylitol with a microorganism, whereby they are converted into xylitol.

The chromatographic separation is preferably conducted after the desalting is carried out, in order to prevent the Ca ions of the strongly acidic cation-exchange resin for the chromatography from being eliminated by the action of the ionic impurities, i.e., organic acids and inorganic salts.

The desired xylitol can be obtained at a high purity by separating it from the xylitol solution fractionated by the chromatographic separation (Step(4)).

Obtaining xylitol of high purity by separating it from the above-mentioned xylitol fraction can be effected, e.g., by crystallizing by concentration, this being per se a conventional procedure. Such crystallization can be effected by concentrating a xylitol solution until the solid content concentration get to within a range of 35 to 85 g/10 g-water, followed by adding seed crystals and gradual cooling. The xylitol can be obtained at high purity by separation by means of subjecting the resulting precipitated xylitol crystals to an appropriate solid-liquid separation such as filtering, centrifuging or the like. Such obtaining by separation can be also effected by crystallizing by organic solvent addition, this being per se a conventional procedure. In greater detail, when the above-mentioned xylitol fraction is added with a lower alcohol miscible at least with water (an organic solvent) such as methanol, ethanal, isopropyl alcohol or the like, the xylitol soluble sparingly in such alcohol crystallizes out therefrom. The xylitol can also be obtained at high purity by separation by means of subjecting the resulting precipitated xylitol crystals to an appropriate solid-liquid separation such as filtering, centrifirging or the like, as in the case of the crystallizing by concentration described above. Alternatively, the crystallizing by concentration and the crystalling by organic acid addition can be carried out in combination. E.g., the above-mentioned xylitol fraction is first concentrated to some extent, and then added with such organic solvent, whereby the xylitol is crystallized out.

The above has explained an embodiment of the present invention wherein the desalting step is conducted once or in one step (one-step desalting process). Such embodiment may be also conducted with adding a desalting step effected by ion exclusion as a pre-step prior to the above desalting step (two-step desalting process).

The following will explain the desalting steps (Steps (2a) and (2b)) of the two-step desalting process in detail.

As has been explained already with respect to the one-step desalting process, the xylitol solution obtained by removal of the solid matter from a culture broth of a xylitol-producing microorganism, still contains such impurities as organic acids and inorganic salts.

Removal of organic acids is usually effected by means of ion exchange procedures using an ion-exchange resin. Such procedures require such amount of the resin that the organic acids can be thoroughly adsorbed, and the organic acids are adsorbed onto the resin for their removal. Furthermore, in order to re-use the resin, the organic acids adsorbed have to be eluted using plenty of an acid or an alkali, so that a large amount of liquid wastes results, and thus costs for raw materials and treatment of the liquid wastes are generated. Accordingly, it is preferable to use the resin in as little amounts as possible, and if such organic acids can be removed by easier procedures, it is possible to reduce the amount of the resin to be used, which, in turn, enables to lower the cost for xylitol production and therefore, to obtain commercially xylitol more easily and more inexpensively.

This has been enabled by the two-step desalting process wherein desalting by means of the ion-exclusion chromatography (Step (2a)) is conducted prior to the desalting step conducted with a cation-exchange resin and an anion-exchange resin in the above-explained one-step desalting process (Step(2b)). By the way, as is well known, when an ion-exchange resin is dipped in an electrolytes solution, electrolytes having the counter ions of the ion-exchange resin are excluded in accordance with the Donnan exclusion and thereby inhibited from entering into the ion-exchange resin. On the other hand, nonelectrolytes can enter into the ion-exchange resin without exclusion by the resin. The procedure of recovering a nonelectrolyte-containing fraction is called as ion-exclusion procedure or ion-exclusion chromatography, wherein, that phenomenon being utilized, a solution containing both of electrolytes and nonelectrolytes is charged on a column of an ion-exchange resin, a fraction containing electrolytes excluded by the resin is first eluted, and then a fraction containing nonelectrolytes eluted later from the column is collected.

Desalting in accordance with the ion-exclusion chromatography (Step(2a)) employs a strongly acidic cation-exchange resin, for example, "UBK-550" manufactured by Mitsubishi Chemical Corporation, preferably in the Na-form or $NH_3$-form. A xylitol solution to be subjected to the ion-exclusion chromatography should have a concentration of the total solid or solid content of 10 to 100 g/dl, preferably 25 to 70 g/dl, and is loaded in an amount of 5 to 20%, preferably 5 to 10%, based on the quantity of the resin. Thereby, about 80% of the organic acids, i.e., most of the ionic substances can be removed from the xylitol solution.

The remaining ionic substances are removed according to the desalting of the afore-explained one-step desalting process. Namely, the xylitol solution after subjected to the desalting in accordance with such ion-exclusion chromatography (Step(2a)) is passed through a cation-exchange resin, e.g., "SK-1B" manufactured by Mitsubishi Chemical Corporation, and an anion-exchange resin, e.g., "WA30", whereby such remaining ionic substances are remove from the xylitol solution (Step(2b)).

The two-step desalting process is the same as the one-step desalting process except that the desalting step (Step (2)) of the latter process are replaced with the two desalting steps, i.e., a first desalting step by the ion-exclusion procedure (Step (2a)) as has been described above, and a second desalting step by means of a cation-exchange resin and an anion-exchange resin (Step (2b)), and therefore, will not need any further explanation.

EXAMPLES

The following examples will further explain the present invention.

By the way, quantitative analysis of each component shown below has been carried out on HPLC.

The analytical conditions are as follows:

(a) As for the three kinds of components, i.e., xylitol, arabitol, and xylulose:
Column: HPLC column "Shodex SUGARSC-1211" (6 mmϕ×250 mm)manufactured by Showa Denko K. K.,
Column bath temperature: 60° C.,
Eluent: acetonitrile/water=40/60,
Dtection: RI detector.

(b) As for the three kinds of components, i.e., acetic acid, citric acid and gluconic acid:
Column: HPLC column "YMC YMC-packODS-AM303" (4.6 mmϕ×250 mm)manufactured by YMC Co. Ltd.
Column bath temperature: 20° C.,
Eluent: 0.1M $NaH_2PO_4$ buffer (pH=2.8)/acetonitrile=95/5.
Detection: UV detector (220 nm).

Example 1

One-step Desalting Process, Starting with D-arabitol (1) Formation of Xylitol by Culturing a Xylitol-producing Microorganism, and Removal of the Solid Matter from the Culture Broth of the Xylitol-producing Microorganism (Step(1))

3.7 L of an aqueous culture medium (pH=7.0) containing 2.4%(w/v) of potato dextrose (manufactured by Difco), 3% of yeast extract(manufactured by Difco), 0.5% of meat extract (manufactured by Difco), and 1.5% of glycerol was sterilized by heating at 120° C. for 15 minutes. D-arabitol after sterilized by heating at120° C. for 15 minutes was added to the above culture medium in an amount of 2%(w/v). Onto the culture medium, Gluconobacter oxydans ATCC 621 was inoculated and cultured or incubated with shaking at 30° C. for 3 days. The microbial cells were collected from the resulting culture broth by centrifugation and washed once with a physiological salt solution.

D-arabitol was dissolved in a 0.1M phosphate buffer (pH=6.0) in such amount that the final concentration thereof was 5%(w/v), whereby a solution was prepared in an amount of 320 ml. Using the solution as the base culture medium (reaction solution), the above microbial cells collected and washed were added thereto in an amount of about 10%(w/v) in terms of wet weight. In order to prevent pH decrease of the culture medium during the progress of culturing or incubation (reaction), calcium carbonate was further added in an amount of 2%(w/v). Culturing was conducted with shaking at 30° C. Also, as the carbon source, glucose was added in an amount of 1%(w/v) at the beginning of the culturing, and after 6 hours from the beginning of the culturing, ethanol was added in an amount of 5%(w/v). After 24 hours from the beginning of the culturing, xylitol had been formed in an amount of 4.9 g per one dl of the culture broth (98% yield based on the D-arabitol).

At this point in time, the culturing was terminated, and the resulting culture broth (xylitol enzymatic reaction broth) was subjected to centrifugation to remove the microbial cells and the other insoluble components (solid matter), followed by filtering with a 0.2 μm membrane filter.

The resulting filtrate amounted to 260 ml, which contained xylitol at a concentration of 4.5 g/dl, acetic acid at a concentration of 3.4 g/dl, gluconic acid at a concentration of 1.77 g/dl, and phosphoric acid at a concentration of 0.10 g/dl.

(2) Removal of the Ionic Substances by Means of the Ion-exchange Chromatography (Step(2))

A portion (200 ml) was taken out of the xylitol solution obtained in the previous step (1). The portion was passed first through a column packed with 200 ml of "SK-1BL" (H-form), a cation-exchange resin manufactured by Mitsubishi Chemical Corporation, and then through a column packed with 250 ml of "MARATHON A2MxBD" (OH-form) manufactured by the same company, to desalt it.

The desalted solution recovered amounted to 510 ml, which contained xylitol at a concentration of 1.43 g/dl, and gluconic acid at a concentration of 0.03 g/dl.

(3) Separation of Sugar(s) and the Other Sugar(s) Alcohol(s) by Chromatography (Step(3))

The desalted solutions obtained by repeating the steps (1) and (2) several times were combined and concentrated, whereby a xylitol solution containing the components at the following concentrations. That is, the xylitol at a concentration of 34.5 g/dl, the D-arabitol at a concentration of 0.5 g/dl, and the D-xylulose at a concentration of 0.7 g/dl.

1,300 ml of "UBK-555" (Ca-form), a cation-exchange resin manufactured by Mitsubishi Chemical Corporation, was packed into a column of 5.0 cm diameter fitted with a heat-retaining jacket, onto which 125 ml of the above-mentioned xylitol solution was loaded and developed with deionized water at a flow rate of 9 ml/minute, and the eluate was fractionated or collected between 0.74 RV and 1.2 RV, whereby a solution was obtained in an amount of 540 ml, containing xylitol at a concentration of 8.2 g/dl and D-arabitol at a concentration of 0.1 g/dl.

(4) Obtaining the Xylitol by Separation (Step(4))

A solution containing xylitol at a concentration of 7.5 g/dl and D-arabitol at a concentration of 0.09 g/dl was prepared as in the step (3). A 1,720 ml portion was taken out of the solution and added with active carbon to decolorize it. After the active carbon has been filtrated off, the filtrate was concentrated until the xylitol got to 45 g per 10 g of water in concentration. After concentrating, the concentrate was added with seed crystals of xylitol, and was gradually cooled from 60° C. to 25° C. over a period of about 3.5 hours while controlling the temperature. It was then stirred overnight to complete crystallization of the xylitol.

After completion of the crystallization, the crystals were separated, washed with a small amount of water, and dried, to give crystalline xylitol in an amount of 80.1 g in a 99.1% purity. The crystals contained 0.9% of moisture, but no other contaminants were confirmed, and therefore they were found to be highly pure crystalline xylitol.

Example 2

One-step Desalting Process, Starting with the D-arabitol Fermentation

Onto YM culture medium manufactured by Difco, Debaryomyces hansenii var. hansenii IFO 0060 strain was inoculated and was cultured or incubated at 30° C. for 3 days.

A culture medium (pH=6.0) containing 10% of D-glucose, 0.5% of peptone, 0.1% of $KH_2PO_4$, 0.05% of $MgSO_4$, and 0.2% of yeast extract was sterilized by heating at 120° C. for 15 minutes. After sterilization, 2%(w/v) of $CaCO_3$ sterilized separately was added thereto, in order to prevent the decrease of the medium pH during the progress of culturing. Onto the culture medium, the above-mentioned culture solution was inoculated in an amount of 10%(v/v), and was cultured at 30° C. On the third day of the culturing, D-arabitol had been formed at a concentration of 3.6 g/dl (36% yield based on the D-glucose).

With the exception that the base culture medium at the step (1) in Example 1 was replaced with 1,000 ml of the resulting D-arabitol fermentation broth, similar procedures were carried out as described in the example, whereby highly pure crystalline xylitol was finally obtained in an amount of 15.8 g.

Example 3

Two-step Desalting Process, Starting with D-arabitol (1) Formation of Xylitol by Culturing a Xylitol-producing Microorganism, and Removal of the Solid Matter from the Culture Broth of the Xylitol-producing Microorganism (Step (1))

The same operation was conducted as in the step (1) of Example 1, whereby the insoluble components (solid matter) was removed, and the remainder was then passed through a membrane filter to obtain a filtrate (the one having a similar composition to the filtrate at the step (1) in Example 1).

(2) Exclusion of the Ionic Substances by the Ion-exclusion Procedure (Step (2a))

1,700 ml of "UBK-550" ($NH_3$-form obtained by replacing the Na-form with aqueous ammonia) manufactured by Mitsubishi Chemical Corporation was packed into a column of 5.6 cm diameter. Thereonto was loaded 110 ml of an aqueous xylitol solution containing 45.1 g/dl of xylitol, 0.5 g/dl of D-arabitol, 5.9 g/dl of citric acid, and 11.0 g/dl of gluconic acid, which aqueous solution had been obtained by concentrating the filtrate obtained at the step (1), and was developed with deionized water at a flow rate of 8 ml/minute.

As shown later in FIG. 1, the xylitol, the arabitol, and the organic acids were separated to recover an aqueous xylitol solution in an amount of 580 ml and containing 6.9 g/dl of xylitol, 0.08 g/dl of D-arabitol, 0.06 g/dl of citric acid, and 0.64 g/dl of gluconic acid.

(3) Removal of the Ionic Substances by the Ion-exchange Chromatography (Step (2b))

After a first-step desalting had been conducted in accordance with the ion-exclusion procedure, following the previous step (2a), a second-step desalting was carried out, according to a conventional method, using a cation-exchange resin and an anion-exchange resin as described in the step (2) of Example 1.

(4) Separation of Sugar(s) and the other Sugar Alcohol(s) by Chromatography (Step (3))

A xylitol solution having the same composition as that at the step (3) of Example 1, i.e., a xylitol solution containing 34.5 g/dl of xtlitol, 0.5 g/dl of D-arabitol, and 0.7 g/dl of D-xylulose, was obtained by repeating the steps (1) to (2b).

Onto a column of 5.0 cm diameter fitted with a heat-retaining jacket and packed with 1300 ml of "UBK-555" (Ca-form), a cation-exchange resin manufactured by Mitsubishi Chemical Corporation was loaded 125 ml of the above-mentioned xylitol solution and developed with deionized water at a flow rate of 9 ml/minute. The eluate was collected between 0.74 RV and 1.2 RV, whereby a solution obtained in an amount of 540 ml, containing 8.2 g/dl of xylitol and 0.1 g/dl of D-arabitol, as in the step (3) of Example 1.

(5) Obtaining the Xylitol by Separation (Step (4))

Following the procedure of the step (4) in Example 1, an equal quantity of xylitol of the same purity as at the said step was obtained from a xylitol solution having the same composition as at the step.

Example 4

Two-step Desalting Process, Starting with the D-arabitol Fermentation

A fermentation broth (1,050 ml) of D-arabitol obtained by a fermentation of d-arabitol similar to that of Example 2 was treated as described in Example 2 to obtain 17.4 g of highly pure crystalline xylitol.

What is claimed is:

1. A process for producing xylitol of high purity which comprises the steps of (1) removing solid matter from a culture broth obtained by culturing a xylitol-producing microorganism in an aqueous culture medium, (2) desalting the resulting solid matter-removed culture broth by removing the ionic substances therefrom by means of a cation-exchange resin and an anion-exchange resin, (3) subjecting the resulting desalted solution to chromatography using a strongly acidic cation-exchange resin to separate xylitol from other sugar alcohol(s) and sugar(s) and to obtain a xylitol solution fraction, and (4) obtaining xylitol by separating it at a high purity from the resulting xylitol solution fraction.

2. The process for producing xylitol of high purity according to claim 1, wherein said strongly acidic cation-exchange resin in step (3) is in a Ca-form.

3. The process for producing xylitol of high purity according to claim 2, wherein said culture broth in step (1) is a culture broth obtained by culturing a xylitol-producing microorganism, starting with D-arabitol as the starting material.

4. The process for producing xylitol of high purity according to claim 1 or 2, wherein said culture broth in step (1) is a culture broth obtained by culturing a xylitol-producing microorganism, starting with D-arabitol, D-xylulose, or glucose, as the starting material.

5. The process for producing xylitol of high purity according to claim 1, wherein said culture broth in step (1) is a culture broth obtained by culturing a xylitol-producing microorganism, starting with D-arabitol as the starting material.

6. The process for producing xylitol of high purity according to claim 1, wherein said separating in step (4) comprises crystallizing said xylitol.

7. The process for producing xylitol of high purity according to claim 6, wherein said culture broth in step (1) is a culture broth obtained by culturing a xylitol-producing microorganism, starting with D-arabitol as the starting material.

8. A process for producing xylitol of high purity which comprises the steps of (1) removing solid matter from a culture broth obtained by culturing a xylitol-producing microorganism in an aqueous culture medium, (2a) desalting the resulting solid matter-removed culture broth by removing most of the ionic substances therefrom by means of ion-exclusion chromatography using a strongly acidic cation-exchange resin, (2b) desalting the solution resulting from the ion-exclusion chromatography (partially desalted solution) by removing the remaining ionic substances therefrom by means of a cation-exchange resin and an anion-exchange resin, (3) subjecting the resulting desalted solution to chromatography using a strongly acidic cation-exchange resin to separate xylitol from other sugar alcohol(s) and sugar(s) and to obtain a xylitol solution fraction, and (4) obtaining xylitol by separating it at a high purity from the resulting xylitol solution fraction.

9. The process for producing xylitol of high purity according to claim 8, wherein said strongly acidic cation-exchange resin in step (3) is in a Ca-form.

10. The process for producing xylitol of high purity according to claim 9, wherein said culture broth in step (1) is a culture broth obtained by culturing a xylitol-producing microorganism, starting with D-arabitol as the starting material.

11. The process for producing xylitol of high purity according to claim 8 or 9, wherein said strongly acidic cation-exchange resin in step (2a) is in a Na-form or a $NH_3$-form.

12. The process for producing xylitol of high purity according to claim 11, wherein said culture broth in step (1) is a culture broth obtained by culturing a xylitol-producing microorganism, starting with D-arabitol, D-xylulose, or glucose, as the starting material.

13. The process for producing xylitol of high purity according to claim 11, wherein said culture broth in step (1) is a culture broth obtained by culturing a xylitol-producing microorganism, starting with D-arabitol as the starting material.

14. The process for producing xylitol of high purity according to claim 8 or 9, wherein said culture broth in step (1) is a culture broth obtained by culturing a xylitol-producing microorganism, starting with D-arabitol, D-xylulose, or glucose, as the starting material.

15. The process for producing xylitol of high purity according to claim 8, wherein said culture broth in step (1) is a culture broth obtained by culturing a xylitol-producing microorganism, starting with D-arabitol as the starting material.

16. The process for producing xylitol of high purity according to claim 8, wherein said separating in step (4) comprises crystallizing said xylitol.

17. The process for producing xylitol of high purity according to claim 16, wherein said culture broth in step (1) is a culture broth obtained by culturing a xylitol-producing microorganism, starting with D-arabitol as the starting material.

* * * * *